United States Patent [19]
Amatucci et al.

[11] Patent Number: 5,635,138
[45] Date of Patent: Jun. 3, 1997

[54] APPARATUS FOR IN SITU X-RAY STUDY OF ELECTROCHEMICAL CELLS

[75] Inventors: Glenn G. Amatucci, Raritan; Jean-Marie Tarascon, Martinsville, both of N.J.

[73] Assignee: Bell Communications Research, Inc., Livingston, N.J.

[21] Appl. No.: 373,830

[22] Filed: Jan. 17, 1995

[51] Int. Cl.[6] ............... G01N 23/20
[52] U.S. Cl. ............ 422/104; 378/70; 378/71; 378/79; 378/88; 422/99; 436/79; 324/432
[58] Field of Search ............ 378/70, 71, 73, 378/79, 82, 88; 422/99, 104; 436/79; 324/432

[56] References Cited

U.S. PATENT DOCUMENTS

| | | | |
|---|---|---|---|
| 5,192,629 | 3/1993 | Guyomard et al. | 429/197 |
| 5,296,318 | 3/1994 | Gozdz et al. | 429/192 |
| 5,350,923 | 9/1994 | Bassignana et al. | 378/79 |

OTHER PUBLICATIONS

R. R. Chianelli et al. *J. Electrochem. Soc.* 1978, 125, 1563–1566.
R. Fong et al. *J. Electrochem. Soc.* 1989, 136, 3206–3210.
C. Cartier et al. *Electrochim. Acta*. 1990, 35, 889–898.
C. Mondoloni et al. *J. Electrochem. Soc.* 1992, 139, 954–959.
T. Gustafsson et al. *Electrochim. Acta* 1992, 37, 1639–1643.
Z. Nagy et al. *Rev. Sci. Instrum.* 1994, 65, 2199–2205.
Y. B. Roh et al. *Jpn. J. Appl. Phys.* 1994, 33, 5917–5924.

Dahn et al,. "In situ X-ray diffraction experiments on lithium intercalation compounds", Can. J. Phys., 60 (1982), 307–313.
Tarascon et al., "Electrochemical, Structural, and Physical Properties of the Sodium Chevrel Phases $Na_xMo_6X_{8-y}I_y$(X= S, Se and y=0 to 2)", J. Solid State Chem., 66, (1987), 204–244.
Li et al., "In situ X-ray diffraction and electrochemical studies of $Li_{1-x}NiO_2$" Solid State Ionics 67 (1993), 123–130.

*Primary Examiner*—Arlen Soderquist

[57] ABSTRACT

An apparatus and method for monitoring structural changes of an electrode in a rechargeable battery include an in situ x-ray study electrochemical cell holder (30) comprising top and bottom cell holder members (32, 34) including at least one beryllium window element (36) for transmission of diffractometer x-radiation. A rechargeable battery cell (43) mounted within the x-ray cell holder enclosure comprises an electrolyte/separator element (68) interposed between positive and negative electrodes (64, 66). A current collector element (70) formed of an electrically-conductive open-mesh grid is disposed between the positive electrode and the separator to enable ion-conducting contact of the electrode and separator while maintaining electrical continuity between the electrode and an external x-ray cell holder terminal (54). As a result of this arrangement, the positive electrode need not contact the window element to establish an electrical battery circuit, but may be sufficiently spaced from the window to avoid electrolytic corrosion of the beryllium element. The in situ x-ray electrochemical cell holder and battery cell structure allow for continuous monitoring of the structural changes in electrode materials during charge/discharge cycling.

20 Claims, 8 Drawing Sheets

APPARATUS FOR IN SITU X-RAY STUDY OF ELECTROCHEMICAL CELLS

BACKGROUND OF THE INVENTION

The present invention relates to an apparatus and method for monitoring structural changes of an electrode in a rechargeable electrochemical cell battery, and, more particularly, to an in situ x-ray study apparatus and method utilizing an electrochemical cell holder having a structure and orientation which eliminates corrosion of the beryllium window of the x-ray study apparatus. Even more particularly, the invention relates to a rechargeable electrochemical cell battery structure for use in an in situ x-ray study apparatus.

The battery-monitoring apparatus of the present invention generally includes an electrolytic, or electrochemical cell comprising polymeric film composition electrodes and separator membranes. In particular, the apparatus includes a rechargeable electrochemical battery cell comprising an intermediate electrolyte/separator element containing an electrolyte solution through which ions from a source electrode material move between cell electrodes during the charge/discharge cycles of the cell. The invention is particularly useful for studying the operation of such cells in which one or both of the electrodes comprises a material capable of intercalating mobile ions, e.g., of sodium, potassium, and particularly lithium, and the electrolyte/separator membrane comprises a polymeric matrix made ionically conductive by the incorporation of an organic solution of a dissociable salt which provides ion mobility. Electrolytic battery cells of this type are generally described in U.S. Pat. Nos. 5,192,629 and 5,296,318, the disclosures of which are incorporated herein by reference, and in U.S. patent application Ser. No. 08/160,018, filed 30 Nov. 1993 now U.S. Pat. No. 5,460,904, issued 24 Oct. 1995, each of which is assigned to the assignee of this application.

The rechargeable battery industry is rapidly promoting the use of rechargeable Li-ion technology. In the Li-ion cell, the positive and negative electrodes comprise lithium intercalation compounds which can be viewed as host structures able to reversibly accept guest lithium ions. The structure of the host compound normally includes vacant sites which determine the number of lithium ions that the material can reversibly accept. The more such vacant sites, the greater the capacity (ampere/gram) of a battery cell using such an intercalation electrode. Thus, it is important for researchers working in the rechargeable battery field to have means for determining the factors limiting the number of lithium ions in an intercalation compound, for instance, the structural changes in the host material induced by intercalation or deintercalation of lithium during charge/discharge cycling.

With a technique that provides this information, one may monitor structural changes of intercalation materials as a function of voltage or electrode composition. Additionally, one may directly monitor the self-discharge mechanism within a battery cell, e.g., a $LiMn_2O_4$/electrolyte/C Li-ion cell, caused by the intercalation of lithium ions into the pure $\lambda$-$MnO_2$ phase. Such a technique may also be used to adjust the ratio of positive to negative electrode materials to ensure the optimum composition and efficient operation of a Li-ion system, since continuously monitoring the lattice cell parameters of the positive and negative electrode permits one to know at any time and at any voltage the population of lithium ions in each electrode. As a result, one can adjust the weight ratio of the electrodes in order for the positive electrode to be completely delithiated when the negative is fully lithiated.

An in situ x-ray diffraction apparatus and technique for performing such studies have been described, for example, by Dahn et al., "in situ X-ray diffraction experiments on lithium intercalation compounds", Can. J. Phys., 60 (1982), 307–313. A variation of in situ electrochemical x-ray study apparatus has also been described by Tarascon et al., "Electrochemical, Structural, and Physical Properties of the Sodium Chevrel Phases $Na_xMo_6X_{8-y}I_y$(X=S, Se and y =0 to 2)", J. Solid Sate Chem., 66 (1987), 204–224. In these prior procedures, where it is desired to study the effect of ion intercalation into an electrode material, the electrode layer is preferably disposed as directly as possible in the path of incident x-radiation in order to obtain strong data responses and avoid diffraction data contamination by extraneous cell components. This end was readily accomplished in these earlier systems by placing the electrode layer upon or directly in contact with a beryllium film serving the dual role of x-ray diffraction apparatus window and electrochemical cell current collector by means of which continuous cell cycling could be studied.

As the search for higher capacity and optimization of electrode materials continues, intercalation compounds with high-voltage regions above about 4.3 volts are becoming more important, since, for many layered intercalation materials, up to forty-five percent of the theoretical capacity lies in the region above this 4.3 volt threshold. Unfortunately, however, the study and analysis of these materials necessary for improving capacity have not previously been available with an in situ electrochemical cell x-ray study apparatus. A major problem, as described by Li et al., "In situ X-ray diffraction and electrochemical studies of $Li_{1-x}NiO_2$", Solid State Ionics, 67 (1993), 123–130, arises from the fact that, particularly when a positive cell electrode layer under study is placed in contact with the diffraction apparatus window, the beryllium film suffers extreme corrosion at cycling potentials in excess of about 4.3 volts, thus severely limiting the utility of the apparatus.

Due to this limitation, the structural variations in these potentially useful intercalation materials could only be determined in isolation by delithiating a different sample at each voltage level in an operating cell cycle. Useful test results could only be obtained with great difficulty in this manner and could seldom be correlated with any degree of reliability. The continuous, high-voltage method and apparatus of the present invention, however, have obviated these limitations and have enabled effective study and development of high capacity electrochemical cell electrode materials.

SUMMARY OF THE INVENTION

The invention comprises an enclosed in situ study electrochemical cell holder having an x-ray transmission window, preferably of beryllium, and means for mounting an electrolytic cell within the enclosure in the path of incident x-radiation transmitted by the window while preventing contact between the window and a high-voltage electrode of the electrolytic cell.

The invention also comprises an electrolytic cell structure in which a current collector element associated with an electrode, typically the higher voltage positive electrode, is situated away from the outer surface of the electrolytic cell, preferably being embedded at the electrode/separator interface in order to ensure that the electrode is disposed as an outermost element of the cell where it may receive unobstructed exposure to the incident x-radiation. The current collector element preferably extends beyond the perimeter of the overlying electrode to provide electrical continuity to an cell holder body terminal and permit the electrode to be separated from the beryllium window which could otherwise suffer destructive electrolytic corrosion.

A preferred in situ x-ray electrochemical cell holder apparatus of the present invention comprises a holder bottom member and a holder top member which has a beryllium window and is operatively attached to, yet electrically insulated from, the bottom member to form an enclosure within the apparatus. The invention further includes, operatively situated in the enclosure between the holder bottom and top members, a polymeric rechargeable battery structure comprising an electrolyte/separator element disposed between positive and negative electrodes having electrical connection to terminals associated with the x-ray cell holders members. In order to receive direct exposure to incident x-radiation, the battery holder is situated such that the electrode to be examined is facing the cell holder window and, when that electrode constitutes the higher voltage positive element of the battery, is maintained at a distance therefrom by interposed spacing means.

The rechargeable battery structure normally also comprises at least one current collector element, typically disposed between the positive electrode and the separator element, through which electrical communication is maintained between the electrode and the holder top member terminal. The current collector is preferably formed of an electrically-conductive open-mesh grid in order to ensure ion mobility between the electrode and the electrolyte/separator element. The negative battery electrode is electrically connected to the cell bottom member terminal either directly, such as by contact with a conductive bottom member, or through a second battery current collector element.

In another embodiment, the electrochemical cell holder also includes a beryllium window in the holder bottom member. The negative electrode is situated to face this second window and, depending upon its electrical potential in the battery, either contacts or is spaced a distance from the window. In the latter arrangement, a second current collector formed of electrically-conductive open-mesh grid disposed between the negative electrode and the separator element maintains electrical circuit with the holder bottom member terminal.

A method in accordance with the present invention comprises the steps of providing an in situ study electrochemical cell having at least one beryllium window in a cell enclosure member; mounting within the cell holder a rechargeable electrochemical battery cell comprising at least one outwardly-disposed electrode having a contiguous current collector element, the electrode facing toward and being separated from the beryllium window and the collector maintaining electrical communication with an electrical terminal on the cell holder; directing x-radiation onto the electrode in reflective incidence through the window; and intercepting reflected x-radiation to obtain diffraction data. The method may alternatively include providing an in situ x-ray study cell holder having two beryllium windows situated respectively in each of a holder top and bottom member; placing the outwardly-disposed positive battery electrode in spaced facing relationship with one window; placing the outwardly-disposed negative battery electrode in spaced facing relationship with the other window, the negative electrode maintaining electrical communication with an electrical terminal on the x-ray cell by direct contact with the other window or through a contiguous current collector element; and selectively situating one or the other window in incident x-radiation to obtain diffraction data from one or the other of the electrodes.

A method in accordance with the present invention for preparing a battery cell structure to be used in the in situ x-ray study apparatus comprises the steps of arranging, in sequence, a positive electrode element, an electrically-conductive open-mesh grid positive current collector element, an electrolyte/separator element, and a negative electrode element, and bonding the electrode and separator elements to adjacent such elements and to the contiguous collector by the application of heat and pressure to form a unitary flexible laminate structure. Alternatively, the positive electrode element and collector element may be so bonded prior to arranging and bonding the balance of the structure elements. The method further comprises including an ion-conductive electrolyte in at least the electrolyte/separator element to form an active electrolytic battery. In a preferred embodiment, the method comprises forming each of the electrodes and electrolyte/separator element as a flexible, self-supporting, film of polymeric composition comprising a compatible organic plasticizer, and, subsequent to bonding, replacing at least a portion of the plasticizer with a solution of ion-conductive electrolyte.

An advantage of the present invention is its simplicity, which ensures that the beryllium window does not experience the corrosion problems of the related art. Another advantage is that the apparatus and method for monitoring structural changes in a rechargeable battery may be used to analyze both the positive and negative electrodes.

BRIEF DESCRIPTION OF THE DRAWING

The present invention will be described with reference to the accompanying drawing of which.

DESCRIPTION OF THE INVENTION

Figure 1:
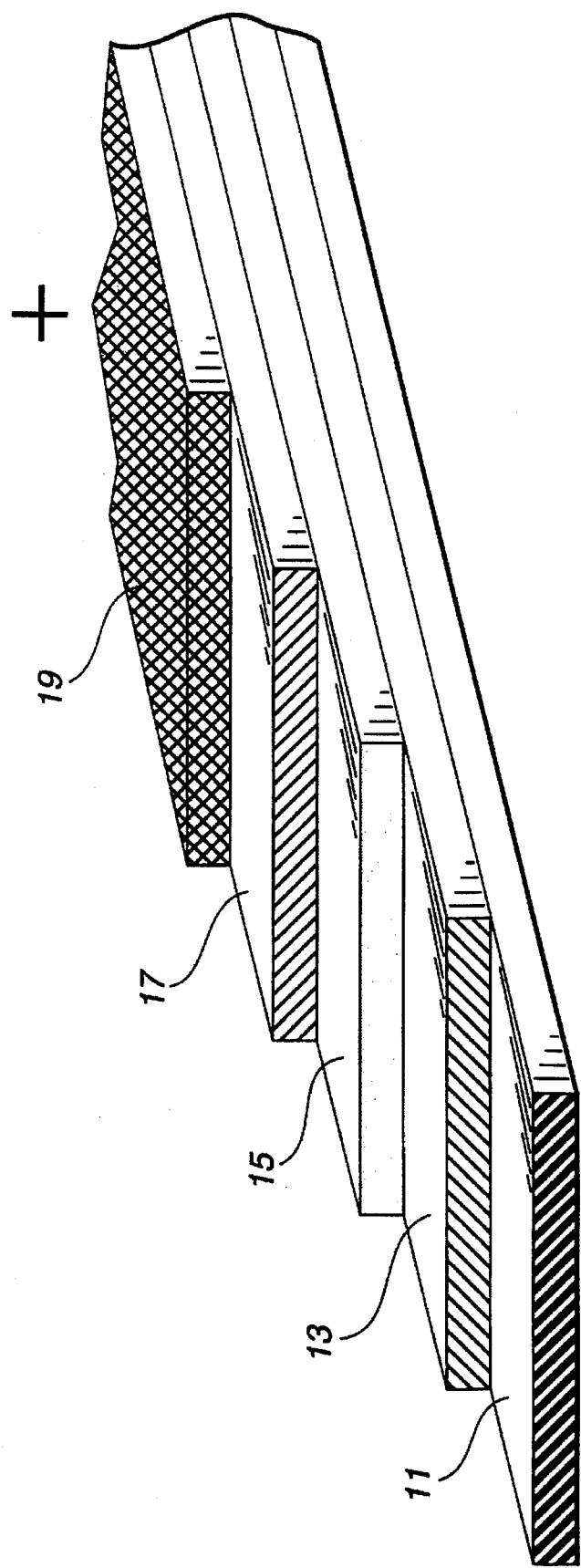
FIG. 1 is a perspective view, in partial section, of a typical laminated Li-ion battery cell structure.

FIG. 1 illustrates a laminated rechargeable battery cell structure of the type currently under development in the industry. This typical Li-ion cell structure comprises a negative current collector 11 of copper foil or grid upon which is laid a negative electrode membrane 13 comprising an intercalatable material, such as carbon or graphite, or a low-voltage lithium insertion compound, such as $WO_2$, $MoO_2$, or Al, dispersed in a plasticized polymeric binder matrix. An electrolyte/separator membrane 15, e.g., a plasticized VdF:HFP copolymer film, is positioned upon electrode element 15 and is covered with a positive electrode membrane 17 comprising a composition of a finely-divided lithium intercalation compound, such as $LiMn_2O_4$, $LiCoO_2$, or $LiNiO_2$, in a similar polymeric binder matrix. An positive current collector 28 of aluminum foil or grid completes the assembly, which is then pressed between platens (not shown) under heat and pressure to soften and bond the polymeric components and laminate the membrane layers and collector elements. Prior to use, the battery is activated by extracting at least a portion of the plasticizer with a selective solvent that does not affect the polymer and replacing the plasticizer with a solution of lithium salt electrolyte, or simply by displacing the portion of plasticizer by contact with the electrolyte solution. Useful electrolyte solution compositions include those described in the incorporated patent disclosures, particularly such compositions as $LiPF_6$ and mixtures with $LiBF_4$ dissolved in mixtures of ethylene carbonate and dimethyl carbonate.

Separator membrane element 15 is generally prepared from a composition comprising a flexible polymer, e.g., a copolymer of 75 to 92% vinylidene fluoride: 8 to 25% hexafluoropropylene (available commercially from Atochem North America as Kynar FLEX), and a compatible organic plasticizer. Such a polymeric composition is also preferred for the preparation of the electrode membrane elements, since subsequent laminate interface compatibility is ensured. The plasticizer may be one of the various organic compounds commonly used as solvents for electrolyte salts, e.g., propylene carbonate or ethylene carbonate, as well as mixtures of these compounds. Higher-boiling plasticizer compounds, such as dibutyl phthalate, dimethyl phthalate, diethyl phthalate, and tris butoxyethyl phosphate are particularly suitable.

Inorganic filler adjuncts, such as fumed alumina or silanized fumed silica, may be used to enhance the physical strength and melt viscosity of a separator membrane and, in some compositions, to increase the subsequent level of electrolyte solution absorption. Other organic polymers and copolymers may be used for the battery electrode and/or the separator. These may be selected from polymers and copolymers such as vinyl chloride, acrylonitrile, vinyl chloride and vinylidene chloride, vinyl chloride and acrylonitrile, vinylidene fluoride, vinylidene fluoride with hexafluoropropylene, and vinylidene fluoride with hexafluoropropylene and an additional component selected from vinyl fluoride, tetrafluoroethylene, and trifluoroethylene.

Any common procedure for casting or forming films or membranes of polymer compositions may be employed in the preparation of these membrane materials. Where casting or coating of a fluid composition is used, e.g., with meter bar or doctor blade apparatus, the viscosity of the composition will normally be reduced by the addition of a readily evaporated casting solvent, such as tetrahydrofuran (THF), acetone, or the like. Such coatings are normally air-dried at moderate temperature to yield self-supporting films of homogeneous, plasticized polymer compositions. A membrane material, particularly for use as a separator element, may also be formed by allowing the polymer in commercial form, i.e., bead or powder, to swell in a proportionate amount of plasticizer and then pressing the swollen mass between heated (e.g., about 130°C.) plates or rollers, or extruding the mixture.

The aluminum grid on the positive electrode, or cathode, of the above-described battery cell structure could be used as the positive current collector of an in situ x-ray study electrochemical cell holder in place of the beryllium window typically used for this purpose. However, in doing so, the x-ray scattering due to aluminum prevents a useful arrangement, because too much of the cathode will be hidden by the aluminum grid. The aluminum causes Bragg peaks in the powder x-ray diffractogram which would greatly obscure the desired data of the electrode material under examination. Thus, such use of the usual rechargeable battery cell structure does not solve the problem of beryllium window corrosion within an in situ x-ray study electrochemical cell holder. In order to ensure that a beryllium window of a cell holder cell does not experience corrosion causing potentials, the present invention provides an air gap between the window and the cathode layer of a battery cell structure and provides the necessary current collector within the battery itself.

Figure 2:
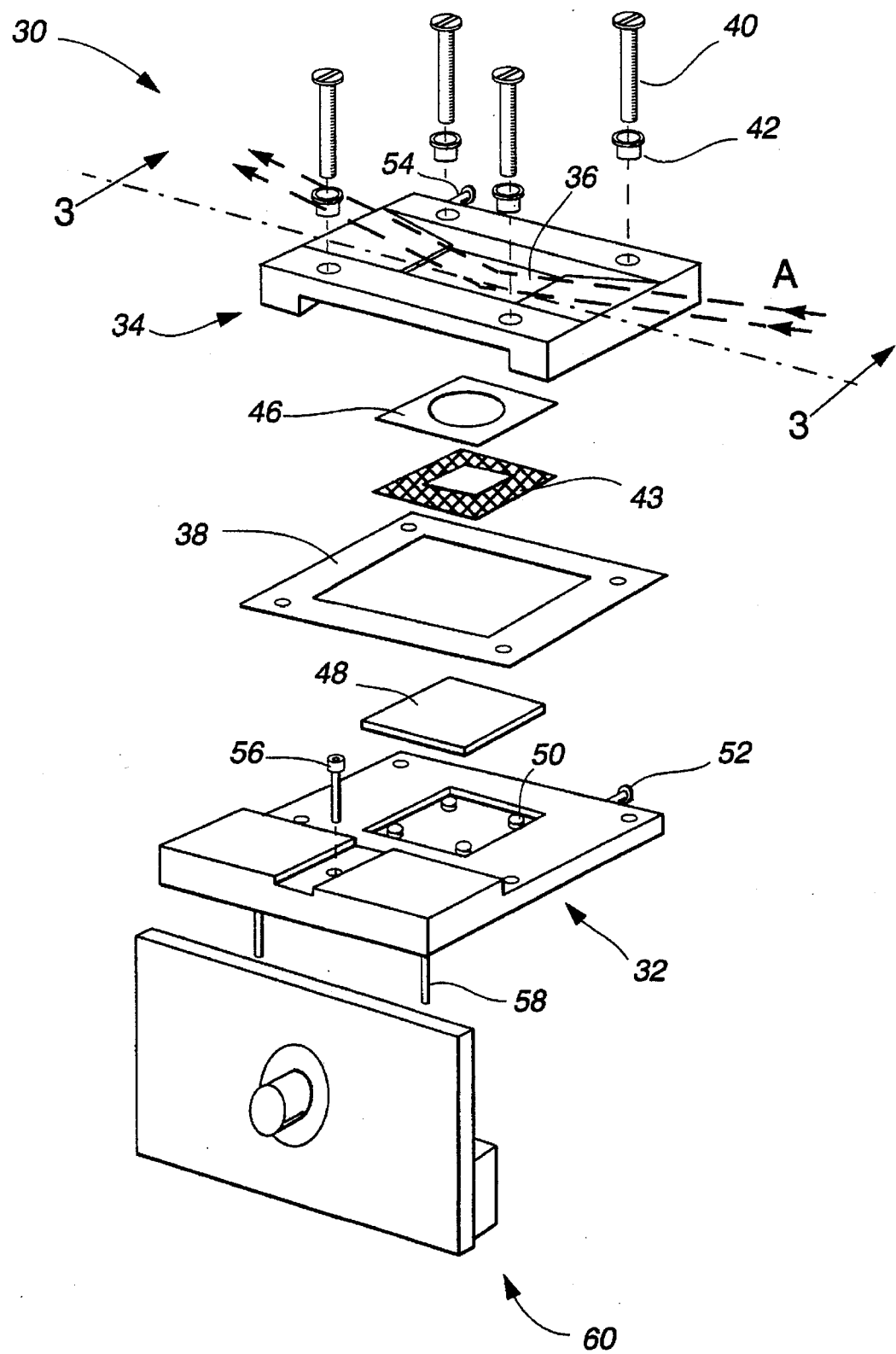
FIG. 2 is an exploded perspective view of an apparatus in accordance with a preferred embodiment of the present invention for monitoring structural changes in a battery cell.

An exemplary embodiment of an in situ x-ray study cell holder useful in the present invention is similar to that described in the above-referenced paper by Tarascon et al. and is shown here in FIG. 2. The holder 30 comprises a holder bottom member 32 and a holder top member 34, generally of metal, operatively connected by means of screws 40 to form an enclosure to accommodate an electrolytic battery cell element 43, such as described later with respect to FIG. 4. Holder top member 34 has a beryllium window 36 to permit x-rays, indicated by arrows A, to enter and exit the cell holder 30. A polyethylene gasket 38 electrically separates top member 34 from bottom member 32, and plastic sleeves 42 maintain the electrical insulation when conductive screws 40 are used. The holder members 32, 34 have respective electrical terminals 52, 54 to provide electrical access to battery electrodes, as later described.

A battery 43 is placed in the enclosure of cell holder 30 between members 32, 34. To ensure a gap between the high voltage terminal of battery 43 and the beryllium window 36, a spacer 46 may be inserted between member 34 and battery 43. The spacer 46 is preferably made of 420 or 430 stainless steel. A copper block 48 may be used to electrically connect the holder bottom 32 to the battery 43. Where necessary, springs 50 may be included to apply pressure to the electrochemical cell holder elements. Cell holder 30 further includes an off-axis adjustment screw 56 and cell aligner pins 58 associated with a nylon holder attachment 60 typically provided with the basic x-ray equipment, e.g, a Rigaku Miniflex diffractometer.

Figure 3:
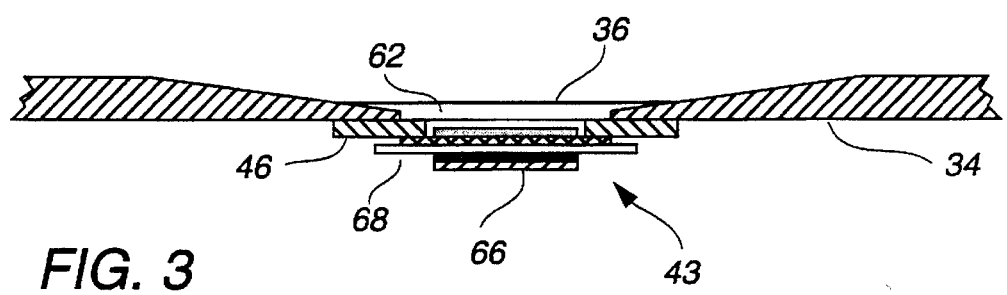
FIG. 3 is a partial cross-sectional view taken along line 3—3 of FIG. 2 showing the cell holder top, spacer, and battery cell.

FIG. 3 shows a partial cross-section of FIG. 2 taken along line 3—3 and better illustrates a gap 62 between the beryllium window 36 and the battery 43 created by a spacer 46 and holder top member 34. It is this gap between the battery 43 and the beryllium window 36 which ensures that there is no contact between the positive battery cell electrode and beryllium window 36 at a potential which causes corrosion. The elimination of such contact with the beryllium window permits the continuous monitoring of the battery electrodes at various stages of charge and discharge.

FIGS. 4–7 show various embodiments of the rechargeable battery cell for use in an in situ x-ray study apparatus in accordance with the present invention. Each of the depicted battery cell structures include a positive electrode 64, a negative electrode 66, and an electrolyte/separator element 68 disposed between the positive and negative electrodes 64, 66. Electrolytic cell electrode and separator elements illustrated in FIGS. 4–7 preferably utilize polymeric materials comprising a composition of poly (vinylidene fluoride) copolymer matrix and a compatible organic plasticizer which maintains a homogeneous composition in the form of a flexible, self-supporting film.

Figure 4:
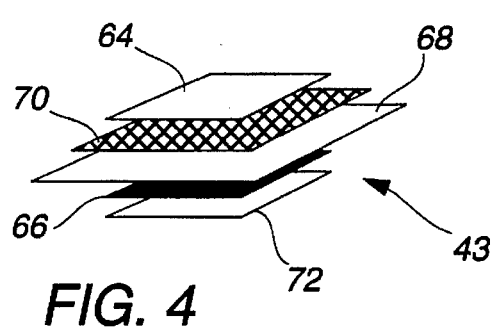
FIG. 4 is an exploded perspective view of a battery structure in accordance with one embodiment of the invention.

FIG. 4 depicts a positive current collector element 70 formed of an electrically-conductive open-mesh grid disposed between positive electrode 64 and separator element 68. Current collector element 70 is preferably made of aluminum and has a perimeter larger than that of positive electrode 64 so as to come into contact with the spacer 46. A second, negative current collector 72, preferably of an electrically conductive copper foil or grid, is placed beneath negative electrode 66 so as to ensure effective electrical contact with copper block 48 of the in situ x-ray study electrochemical cell holder depicted in FIG. 2.

In the embodiment of FIG. 4, the rechargeable battery cell structure 43 is configured according to the invention by means of the lamination of electrode and electrolyte/separator cell elements which are individually prepared, by coating, extrusion, or otherwise, from compositions comprising the noted PVdF copolymer materials. For example, in the construction of a lithium-ion battery, a negative electrode membrane 66 formed as a layer of a powdered carbon dispersion in the polymeric matrix is overlaid upon a copper current collector foil 72. An electrolyte/separator membrane 68 formed as a layer of a composition comprising the described VdF:HFP copolymer and a compatible plasticizer is then overlaid upon negative electrode 66. A positive current collector 70 of open-mesh aluminum grid is overlaid upon separator 68 and the positive electrode membrane 64 separately prepared as a layer of a dispersion of intercalation electrode composition, e.g., a $LiMn_2O_4$ powder in the copolymer matrix, is overlaid upon collector 70 to complete the cell assembly. This assembly is then heated under pressure to bond the plasticized copolymer matrix components and the collector grids to thereby effect the lamination of the cell elements into a unitary flexible battery cell structure. The grid structure of positive current collector 70 allows effective ion-conducting, bonded contact between positive electrode layer 64 and electrolyte/separator membrane 68, the collector grid 70 being thereby, in effect, embedded in the laminate structure at the interface of layers 64, 68. Battery 43 is thereafter activated with electrolyte solution prior to mounted in cell holder 30.

Figure 5:
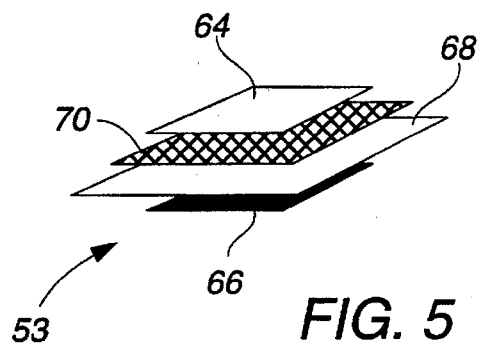
FIG. 5 is an exploded perspective view of another embodiment of a battery cell structure in accordance with one embodiment of the invention.

As shown generally in FIG. 5, an alternative battery cell structure 53 is depicted without the negative current collector 72 of FIG. 4. In use, the negative electrode 66 electrically contacts the cell holder bottom 32 (FIG. 2) either directly or indirectly, such as through the copper block 48. A preferred use for the battery cell of FIG. 5 will be discussed below with reference to FIG. 10.

Figure 6:
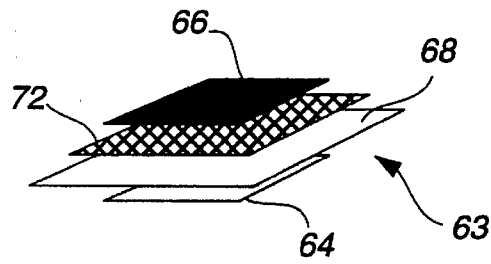
FIG. 6 is an exploded perspective view of yet another embodiment of a battery cell structure.

FIG. 6 illustrates a battery cell 63 adapted for examination of negative electrode materials. A negative open-mesh current collector grid 72, typically of copper, is disposed between negative electrode 66 and separator element 68 with electrode 66 facing and spaced from the window of the cell holder of FIG. 2. This configuration allows a researcher to study the negative electrode 66 and maintain a gap between the beryllium window 36 and the negative electrode 66 so as to prevent any corrosion of the window which might result from excessive electrical potential. The contact block 48 of the x-ray cell would preferably be fashioned of 420 or 430 stainless steel to avoid corrosion of a copper block by positive electrode 64.

Figure 7:
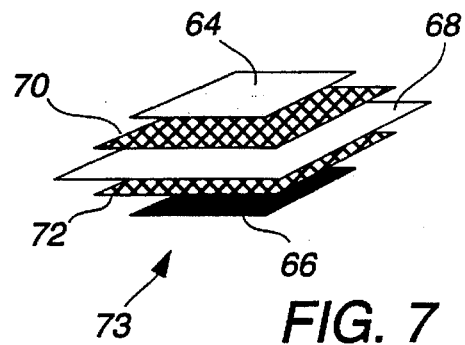
FIG. 7 is an exploded perspective view of a further embodiment of a battery cell structure.

FIG. 7 depicts a battery cell structure 73 having two open-mesh current collectors, the first of aluminum 70 disposed between the positive electrode 64 and separator 68, and the other of copper 72 disposed between the negative electrode 66 and separator 68. As shown, the perimeter of separator 68 extends sufficiently beyond those of collectors 70, 72 to provide effective electrical insulation of the two. This configuration is utilized in an in situ x-ray study cell holder as shown in FIG. 10 which allows for the analysis of both the positive and negative electrodes through a beryllium window located in each of cell holder members 32, 34.

Figure 8:
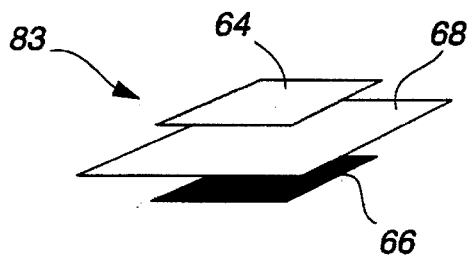
FIG. 8 is an exploded perspective view of another embodiment of a battery cell structure.

FIG. 8 depicts a battery cell structure 83 consisting essentially of positive electrode 64, negative electrode 66, and separator 68 disposed between the two electrodes. This is an extreme design for a rechargeable battery cell member of however, in which positive electrode 64 would be spaced from the beryllium window and contact the spacer 46 or holder top 34 to serve as both the electrode and current collector, although the electrical conductivity would be less than that achieved with an aluminum current collector grid.

Figure 9:
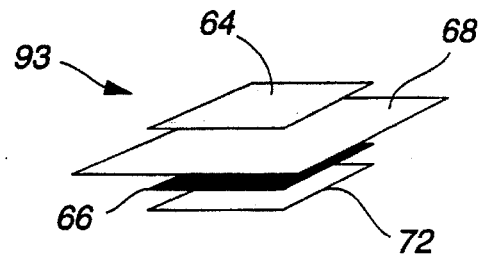
FIG. 9 is an exploded perspective view of yet a further embodiment of a battery cell structure.

FIG. 9 depicts a battery cell variant 93 in which separator 68 is disposed between positive electrode 64 and negative electrode 66 and a negative current collector 72 contacts negative electrode 66 on the opposite side from that of separator 68.

Figure 10:
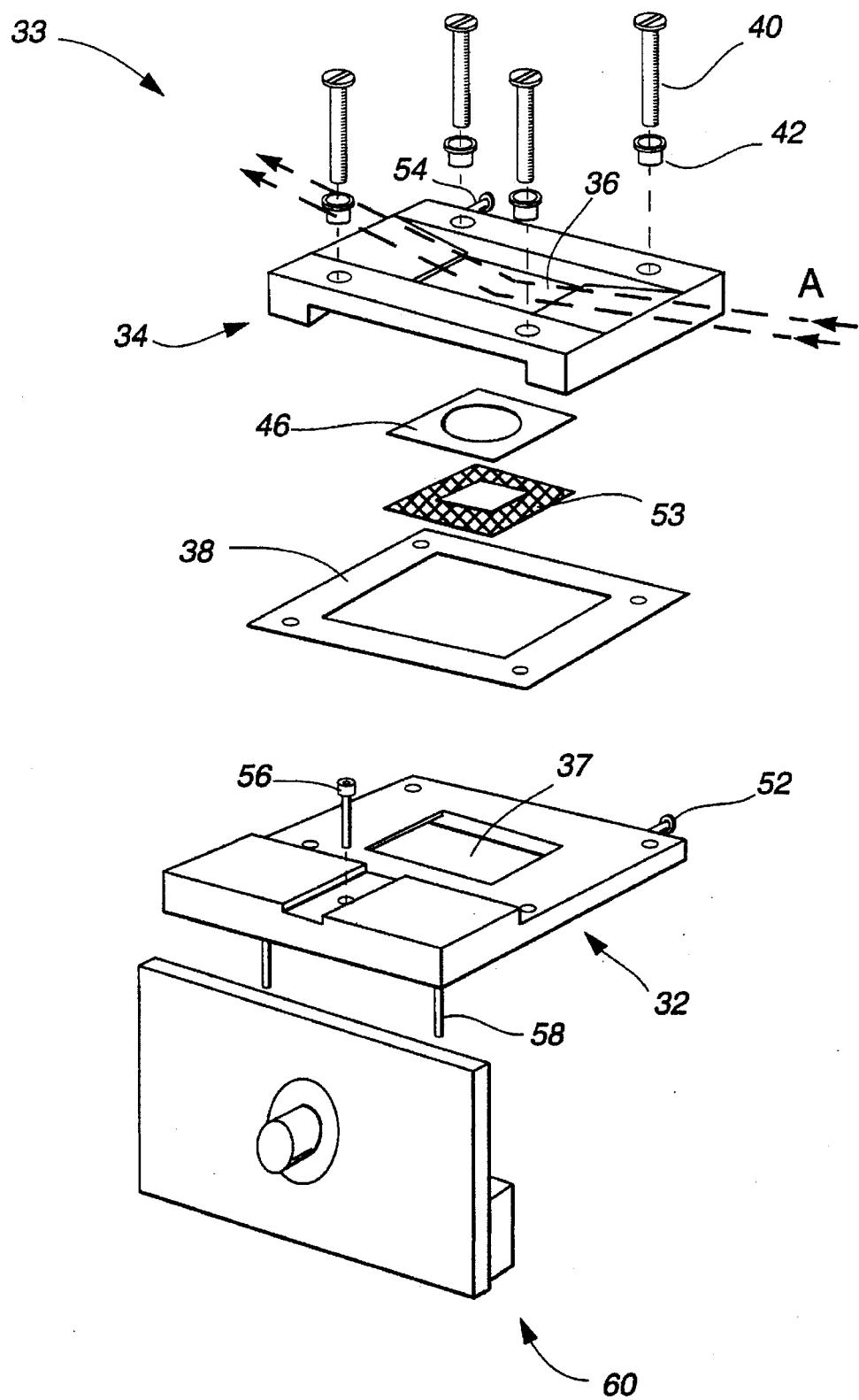
FIG. 10 is an exploded perspective view of an apparatus in accordance with another preferred embodiment of the present invention for monitoring structural changes in a battery cell.

FIG. 10 depicts an in situ x-ray study electrochemical cell holder 33 which is similar to that shown in FIG. 2, except that the holder bottom member 32 provides a second beryllium window 37 to allow for the alternate monitoring of both the positive electrode 64 and the negative electrode 66 of a battery member. X-rays beams are thus permitted, upon rotation of the cell, to enter and exit the respective window exposing the positive or negative electrode. For use in 33, the preferred Li-ion battery cell may be as simply depicted in FIG. 5, since the negative electrode 66 which remains below about 3 volts in a Li-ion cell can be placed directly onto beryllium window 37 which can serve as current collector without risk of corrosion. Determining the voltage of a particular electrode allows one to determine when use a battery member with an electrode, separator, and grid configuration that provides for maintaining a gap between the beryllium window and the electrode, and when one may simply place the electrode directly upon the beryllium window itself.

An x-ray study cell holder 30 of FIG. 2, or 33 of FIG. 10, is preferably assembled with an activated rechargeable battery cell in a helium-filled dry box, then placed in an x-ray diffractometer to perform the analysis experiment. In the diffractometer, the cell holder cell is aligned by means of a screw 56 which moves back and forth along the cell aligner pins 58. In addition, the cell holder 33 of FIG. 10 can be rotated 180° using the diffractometer Phi to expose one and the other of the electrodes of the battery to incident x-radiation at any time during charge/discharge cycling.

To ensure that each respective electrode 64, 66 is aligned correctly upon rotation of cell holder 33, an adjustable out-of-center rotation is used. Since, in FIG. 5 for example, current collector 70 is embedded in battery cell 53 and a negative collector is not included the battery will only be a few hundred micrometers thick e.g., 300–400 µm. Thus, if the positive electrode 64 is in perfect x-plane alignment, the negative electrode 66 will only be a few hundred µm off in the alignment after x-ray cell 33 is rotated. This will have moderate effect on the peak data intensities, but the shift in these spacings can easily be corrected by an off-axis adjustment. For instance, if the battery is 300 µm thick and the positive electrode is in perfect alignment, rotation would result in a 300 µm off-axis for the negative electrode. Thus, the positive electrode is adjusted to be 150 µm off-axis in order that rotation results in the negative electrode being likewise only 150 µm off-axis.

The assembled cell holder may be mounted on any suitable diffractometer, e.g, a system commercially available from Rigaku or Scintag. The positive and negative terminals 52, 54 which are maintained in electrical continuity with battery electrodes 64, 66 are connected to a battery cycler that is driven by a computer for controlled charge and discharge of the battery. Measurement data of the x-ray diffraction patterns are collected within the range of $10<2\theta<90$ while the cell is charged and discharged at a constant current. Usually a current of 140 µA is used and x-ray diffraction data are automatically collected when x in $Li_xMn_2O_4$ changes by about 0.02. Therefore, more than 50 x-ray powder diffractograms may be collected for a single charge cycle. The same may be done during discharge. The current rate is maintained low in order to maintain nearly equilibrium conditions and detect small structural changes.

Figure 11:
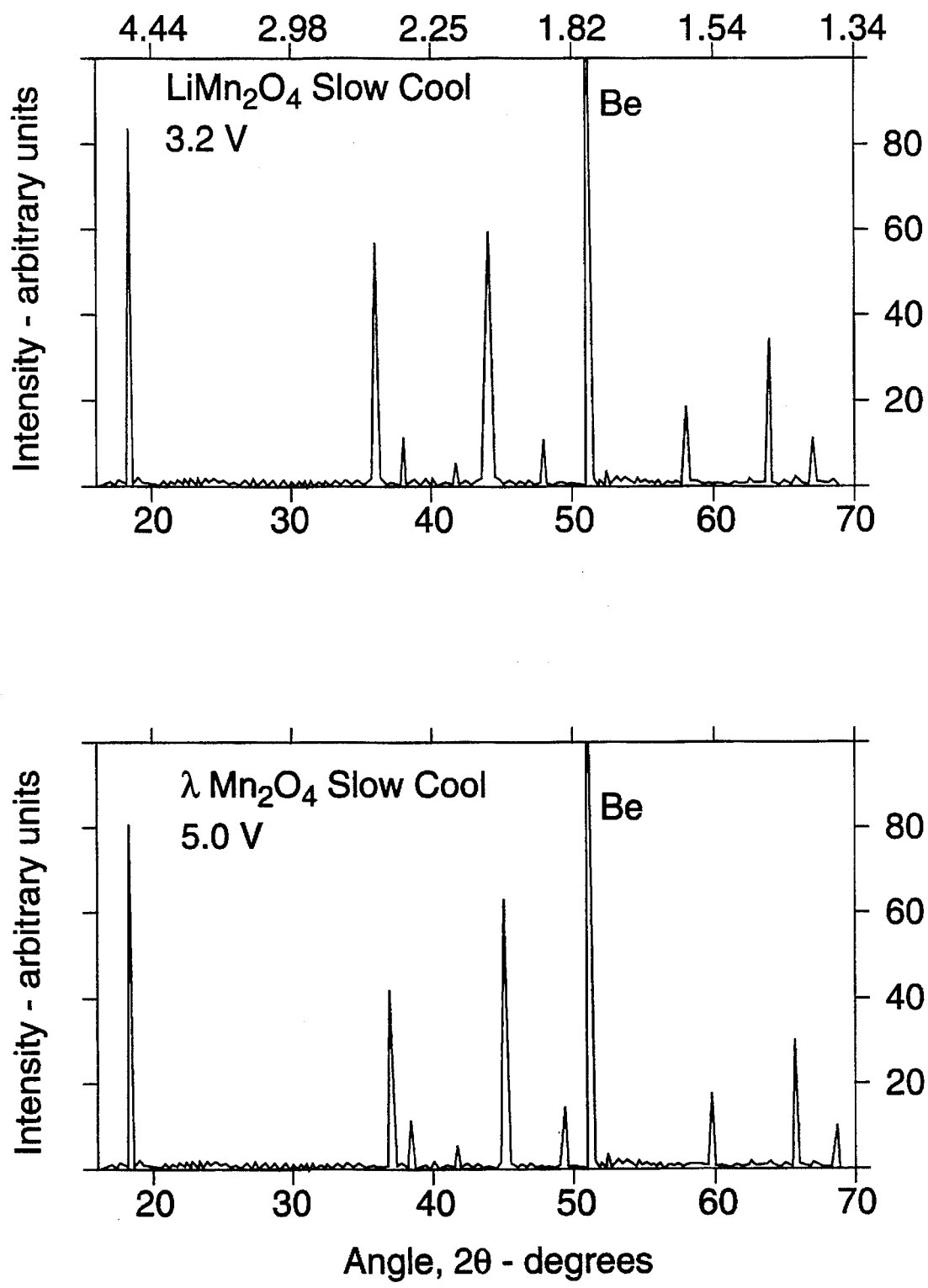
FIG. 11 is a graph showing experimental results derived from using one embodiment of the present invention.
Figure 12:
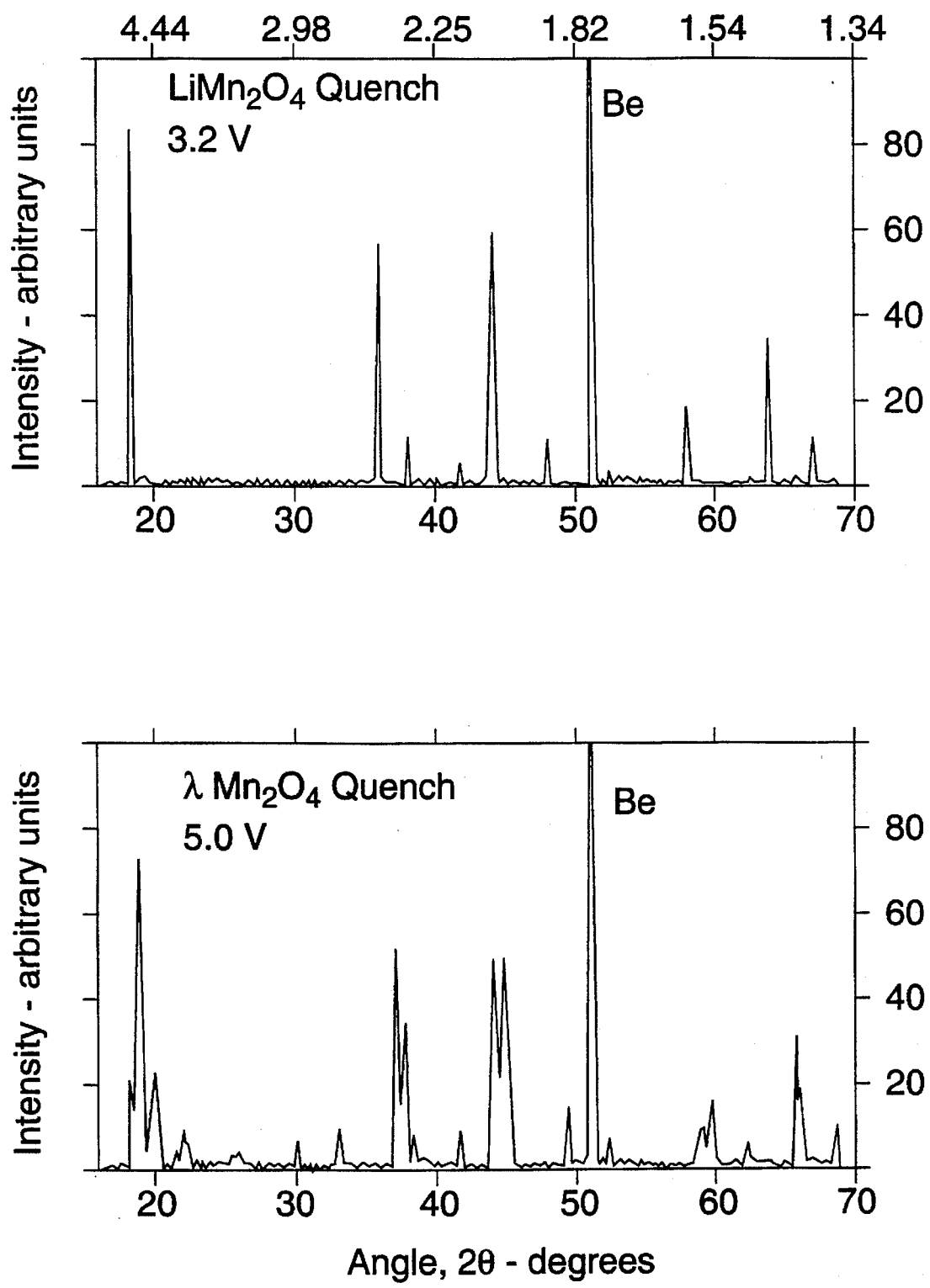
FIG. 12 is a graph showing additional experimental results derived from using one embodiment of the present invention.

The results of studies utilizing the present invention are illustrated in the graphs of FIGS. 11–15. It may be noted in the x-ray diffraction patterns of FIGS. 11–12 that the structure of a final delithiation product, $\lambda$-$MnO_2$, is influenced significantly by the manner in which the starting $LiMn_2O_4$ material was synthesized, e.g., whether during an annealing operation it was low cooled or quenched, as indicated in FIGS. 11 and 12, respectively.

Figure 13:
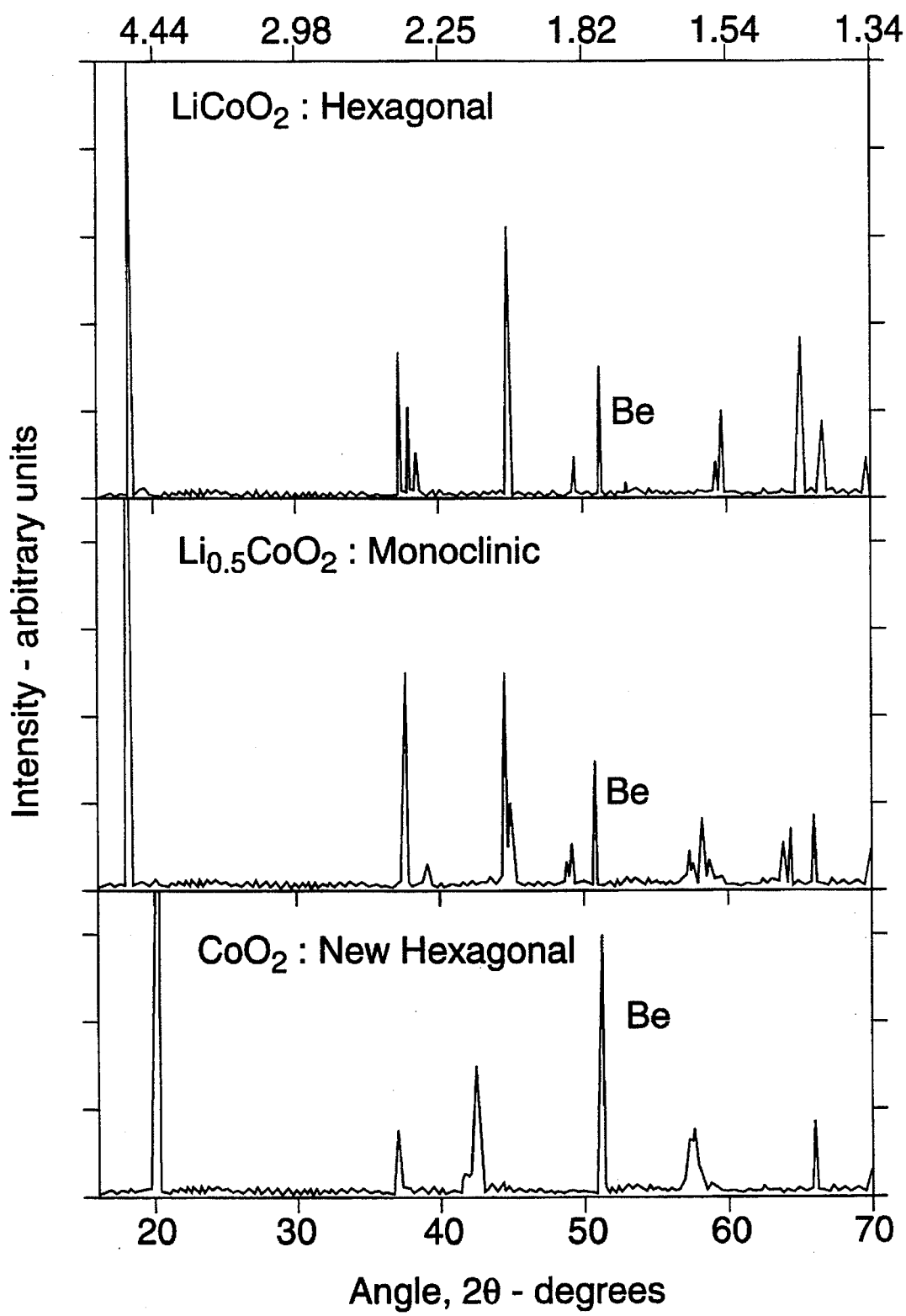
FIG. 13 is a graph showing further experimental results derived from using one embodiment of the present invention.
Figure 14:
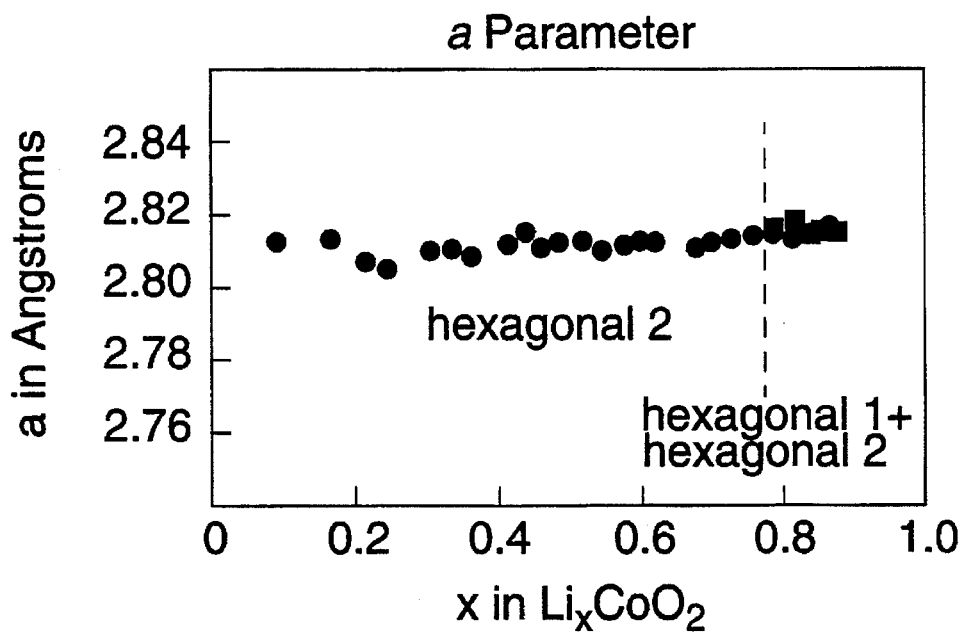
FIG. 14 is a graph showing a-axis parameter experimental results derived from using one embodiment of the present invention.
Figure 15:
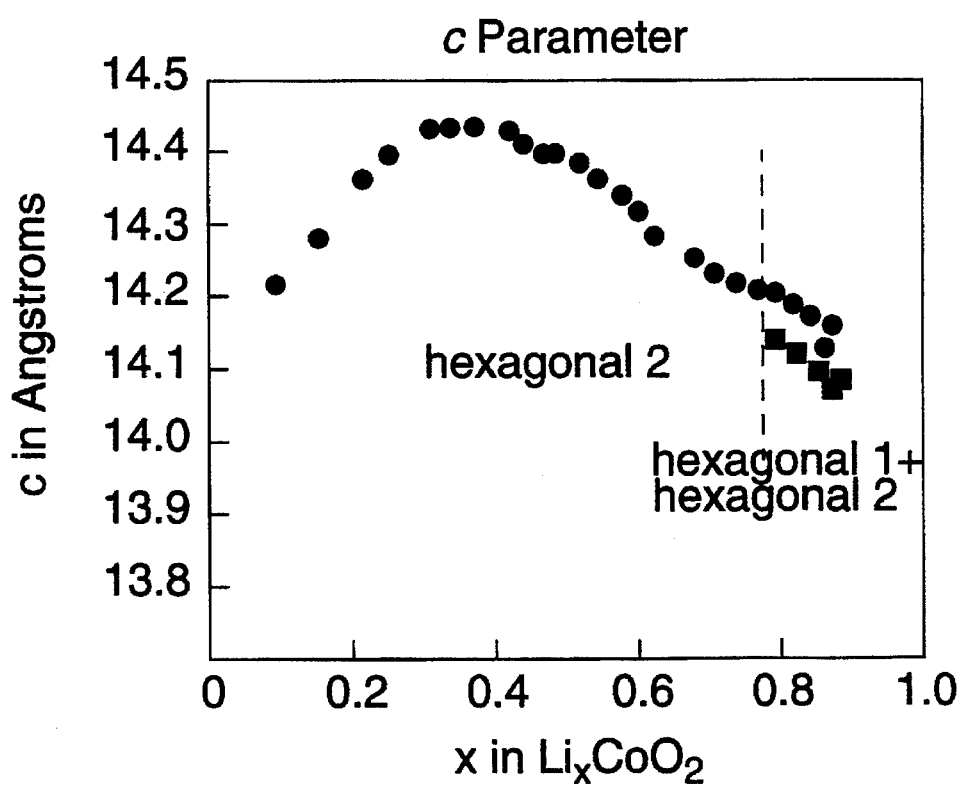
FIG. 15 is a graph showing c-axis parameter experimental results derived from using one embodiment of the present invention.

The effective performance of the in situ x-ray study cell holder with other electrode materials can be seen in the diffraction patterns of various $CoO_2$ compounds, as depicted in FIG. 13. Utilizing the present x-ray cell, voltages were raised up to 5 volts to achieve, without difficulty, compound phases, e.g., of $CoO_2$, which had previously been unattained. FIGS. 14–15 show graphically the results of accumulated test data from which are determined the variations of the crystallographic a- and c-axis parameters as a function of the amount of intercalated lithium in a hexagonal $LiCoO_2$ positive electrode material. While the preferred embodiments of the battery structure have centered on rechargeable Li-ion batteries, it is also well within the scope of the present invention to implement this design with other rechargeable batteries, as well, including aqueous systems.

With the increasing importance of the rechargeable Li-ion technology, it is anticipated that any battery manufacturers or research labs searching for new intercalation electrodes will find this type of research tool to be invaluable. The use of an in situ x-ray study electrochemical cell holder with a specially designed rechargeable battery structure which does not corrode the beryllium window is, among other things, an excellent research tool for obtaining the best cathode, anode, or polymeric component materials. Additionally, research generated from such tests provides ways to characterize final materials used in commercial rechargeable batteries.

While there has been illustrated and described what is at present considered to be a preferred embodiment of the present invention, it will understood by those skilled in the art that various changes and modifications may be made, and equivalents may be substituted without departing from the true scope of the invention. Therefore, it is intended that this invention not be limited to the particular embodiment disclosed herein, but that the invention include all embodiments falling within the scope of the appended claims.

What is claimed is:

1. Apparatus for in situ x-ray study of electrochemical cells which comprises an electrochemical cell comprising a positive electrode, a negative electrode, and an interposed electrolyte/separator element in contact with said electrodes, means for mounting said electrochemical cell in the path of incident x-radiation, said mounting means comprising means enclosing said electrochemical cell which includes at least one window element for transmission of said x-radiation to incidence upon said cell, said enclosing means comprising first and second opposed electrically-conductive members electrically isolated from one another and respectively providing positive and negative electrical terminals characterized in that said mounting means further comprises a) means for electrically connecting said positive electrode to said first conductive member and said negative electrode to said second conductive member; and b) means for maintaining said cell spaced from and out of contact with said window element.

2. Apparatus according to claim 1 characterized in that said electrochemical cell is disposed in said mounting means to present the outer surface of at least one of said electrodes to x-radiation transmitted by said window element.

3. Apparatus according to claim 2 characterized in that said electrochemical cell further comprises a current collector element in contact with and situated away from said outer surface of said at leats one electrode.

4. Apparatus according to claim 3 wherein said collector element is disposed substantially at the interface between, and includes means providing ion-conductive contact between, said at least one electrode and said separator element.

5. Apparatus according to claim 4 wherein said collector element comprises an electrically-conductive open-mesh grid.

6. Apparatus according to claim 3 wherein said collector element is in electrical communication circuit with one of said opposed conductive member terminals.

7. Apparatus according to claim 3 wherein said at least one electrode is the positive electrode of said electrochemical cell.

8. Apparatus according to claim 2 characterized in that said enclosing means includes a second window element situated to transmit x-radiation to incidence upon the outer surface of the other of said electrodes.

9. Apparatus according to claim 8 wherein said electrochemical cell further comprises a second current collector element in contact with said other electrode and in electrical communication with the respective one of said opposed conductive member terminals.

10. Apparatus according to claim 9 wherein said second collector element is disposed substantially at the interface between, and includes means providing ion-conductive contact between, said other electrode and said electrolyte/separator element.

11. Apparatus according to claim 10 wherein said second collector element comprises an electrically-conductive open-mesh grid.

12. Apparatus according to claim 1 characterized in that said electrochemical cell comprises a rechargeable battery structure wherein:

a) each of said electrodes and electrolyte/separator element comprises a flexible, self-supporting, polymeric matrix composition film; and b) each said film is bonded to contiguous films at its respective interface to form a unitary flexible laminate structure.

13. Apparatus according to claim 12 wherein at least said electrolyte/separator comprises an electrolyte providing ion mobility.

14. Apparatus according to claim 12 wherein a current collector element is disposed substantially at the interface between, and includes means providing ion-conductive contact between, said positive electrode and said electrolyte/separator element.

15. Apparatus according to claim 14 wherein said collector element comprises an electrically-conductive open-mesh grid.

16. Apparatus according to claim 12 wherein said positive electrode comprises a lithium intercalation compound homogeneously distributed in a matrix having the polymeric composition of said separator.

17. Apparatus according to claim 16 wherein said intercalation compound has a nominal formula selected from $LiMn_2O_4$, $LiCoO_2$, and $LiNiO_2$.

18. Apparatus according to claim 12 wherein said negative electrode comprises a carbon intercalation compound homogeneously distributed in a matrix having the polymeric composition of said separator.

19. An apparatus comprising:

a) an in situ x-rays study electrochemical cell holder comprising:

1) a cell holder bottom; and 2) a cell holder top operatively attached to said bottom, said top having a beryllium window; and b) a rechargeable battery cell structure comprising:

1) a positive electrode element;

2) a negative electrode element;

3) an electrolyte/separator element disposed between said positive and negative electrode elements; and 4) a current collector element disposed between said positive electrode element and said electrolyte/separator element, said current collector element being formed of an electrically-conductive open-mesh grid, said positive electrode element facing toward and spaced from said beryllium window said negative electrode element electrically contacting said bottom, and said current collector element electrically contacting said top.

20. The apparatus of claim 19 which further comprises a conductive spacer contacting said cell holder top and said current collector element and providing a gap between said beryllium window and said positive electrode element.

* * * * *